United States Patent
Chou et al.

(10) Patent No.: US 11,826,340 B1
(45) Date of Patent: Nov. 28, 2023

(54) METHOD FOR TREATEING OR PREVENTING ISCHEMIC OPTIC NEUROPATHY

(71) Applicant: TZU CHI UNIVERSITY, Hualien (TW)

(72) Inventors: Yu-Yau Chou, Hualien (TW); Jia-Ying Chien, Hualien (TW); Jhih-Wei Ciou, Hualien (TW); Shun-Ping Huang, Hualien (TW)

(73) Assignee: TZU CHI UNIVERSITY, Hualien (TW)

( * ) Notice: Subject to any disclaimer, the term of this patent is extended or adjusted under 35 U.S.C. 154(b) by 0 days.

(21) Appl. No.: 17/831,834

(22) Filed: Jun. 3, 2022

(30) Foreign Application Priority Data

May 18, 2022 (TW) .................................. 111118485

(51) Int. Cl.
*A61K 31/343* (2006.01)
*A61P 25/02* (2006.01)
*A61P 27/02* (2006.01)

(52) U.S. Cl.
CPC ............ *A61K 31/343* (2013.01); *A61P 25/02* (2018.01); *A61P 27/02* (2018.01)

(58) Field of Classification Search
CPC ......... A61K 31/343; A61P 27/02; A61P 75/02
See application file for complete search history.

(56) References Cited

PUBLICATIONS

Chou et al., The Protective Effects of n-Butylidenephthalide on Retinal Ganglion Cells during Ischemic Injury, 23(4) Int. J. Mol. Sci. 2095 (2022) (publ'd Feb. 14, 2022) (Year: 2022).*

* cited by examiner

*Primary Examiner* — Timothy R Rozof
(74) *Attorney, Agent, or Firm* — MUNCY, GEISSLER, OLDS & LOWE, P.C.

(57) ABSTRACT

The present invention provides use of a compound represented by formula (1), and the use is manufacturing a medicine for treating or preventing ischemic optic neuropathy, wherein the formula (1) is as below:

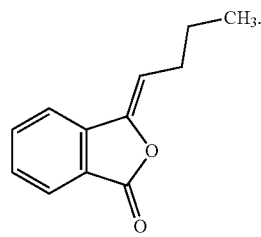

10 Claims, 19 Drawing Sheets
(4 of 19 Drawing Sheet(s) Filed in Color)

METHOD FOR TREATEING OR PREVENTING ISCHEMIC OPTIC NEUROPATHY

This application claims priority to Taiwan Patent Application No. 111118485 filed on May 18, 2022.

CROSS-REFERENCES TO RELATED APPLICATIONS

Not applicable.

BACKGROUND OF THE INVENTION

Field of the Invention

The present invention relates to use of n-butylidenephthalide, and in particular, relates to pharmaceutical use of n-butylidenephthalide.

Descriptions of the Related Art

Ischemic optic neuropathy (ION) is one of the main pathological manifestations of visual impairment and vision loss in ophthalmic diseases; among these diseases, non-arteritic anterior ischemic optic neuropathy (NAION) is the most common type of eye diseases. The majority of NAION patients are middle-aged and elderly individuals over 50 years of age, who usually have an accompanying risk of cardiovascular diseases (hypertension, hypercholesterolemia, nocturnal hypertension, and/or diabetes). Clinically, the most common presentation of NAION in patients includes optic disc swelling and hyperemia, loss of color vision, and visual field defects, eventually leading to visual loss, for which there is still no effective safe treatment. However, the NAION model of rodents (rAION) has long been developed in different types of potential therapeutic trials, so it is imperative to identify appropriate treatments in preclinical studies related to rNAION. Studies have pointed out that poor circulation of the optic nerve (ON) head leads Ato the loss of vascular homeostasis, thus triggering the NAION process. Meanwhile, disc swelling and compartment syndrome can further induce oxidative stress. Oxidative stress promotes the development of neuroinflammation and the loss of retinal ganglion cells (RGCs). However, the complete mechanism constituting the cause of this chain reaction is still unknown. Therefore, reducing the response to neuroinflammation and preventing the loss of RGCs is a priority for preserving visual function.

For a long time, Angelica has been used in Chinese medicinal for the treatment of arthritis and headaches, and has been widely used in pharmacological research as an antipyretic extract. N-butylidenephthalide (BP), as one of the major components of Angelica, has been studied to have various capacities, including antitumor and anti-inflammatory, and neuroprotective effects. Besides, BP combined with other treatments can reduce injury and promote neurogenesis after cerebral ischemic stroke. Related studies on cardiovascular diseases have shown that BP can regulate the inflammatory process by changing the phenotype of macrophage and preventing myocardial fibrosis in rats after infarction. For neurodegenerative diseases, BP prolongs the life of a mouse model of amyotrophic lateral sclerosis (ALS) by inhibiting motor neurons from apoptosis and reducing the development of neuroinflammation.

In summary, BP is a potential candidate for treating ischemic injury, the molecular mechanism of BP is expected to be studied by modulating inflammatory mediators of ischemic optic neuropathy, and the survival rates of RGCs and the recovery of visual function were evaluated to confirm the therapeutic effects of BP.

SUMMARY OF THE INVENTION

The present invention provides use of a compound represented by formula (1) in preparing a medicine for treating or preventing ischemic optic neuropathy, wherein the formula (1) is as below:

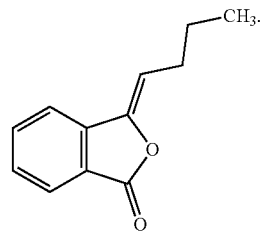 [SMILES: CCC/C=C1\OC(=O)c2ccccc21]

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENT

Figure 1:
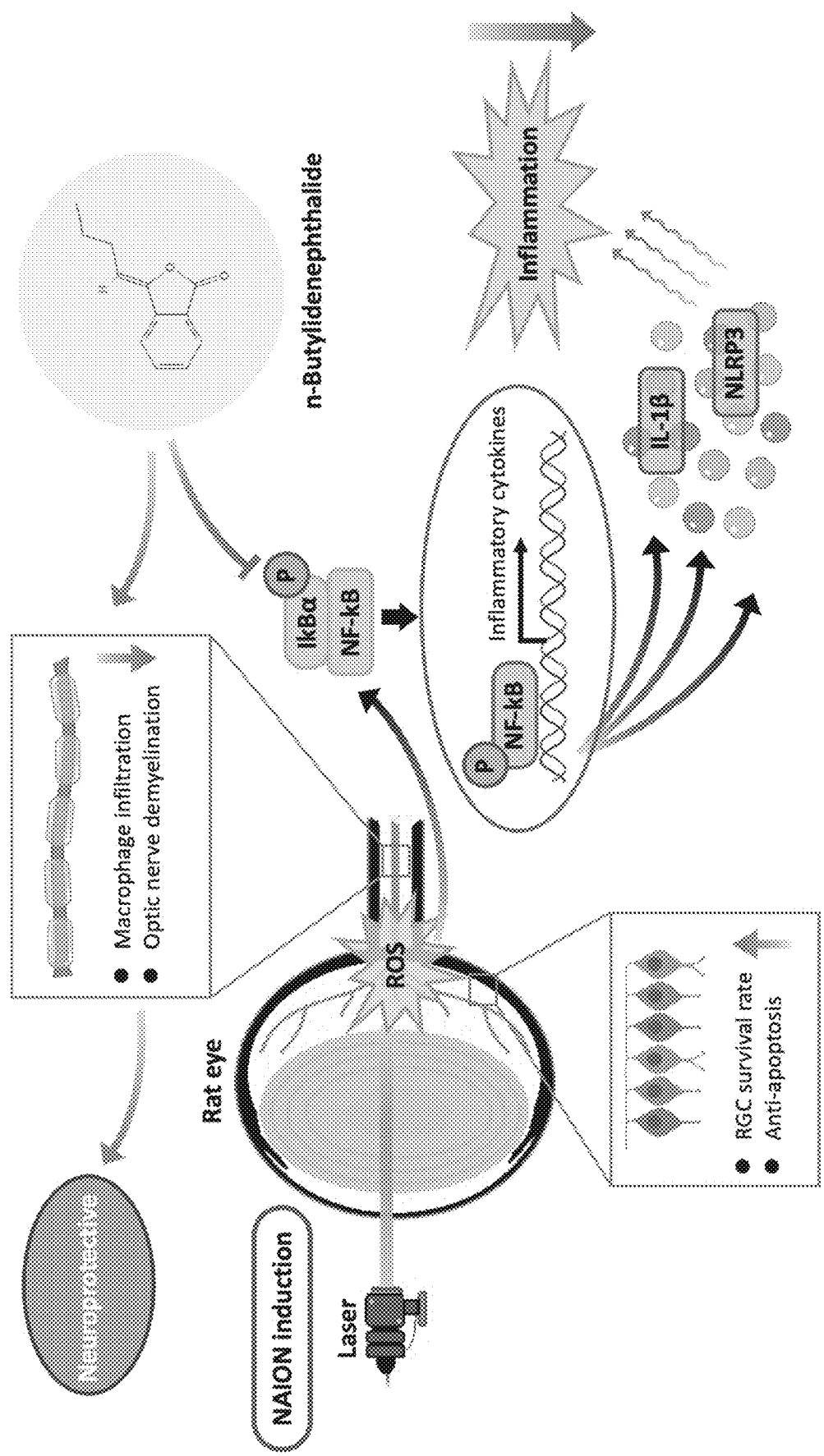
FIG. 1 is a schematic diagram showing the neuroprotective effect of n-butylidenephthalide after AION induction.

To achieve a better understanding of the above and/or other objectives, effects, and features of the present invention, preferred embodiments are described in detail below:

Referring to FIG. 1, it is found that BP can prevent RGCs from undergoing apoptosis and preserve visual function by reducing macrophage infiltration, preventing the process of demyelination, and inhibiting inflammatory cytokines activation. It is also found that BP protects the nerves by regulating the NF-κB signaling pathway. As used, the terms "compound represented by formula (1)" and "n-butylidenephthalide" refer to the same compound and are used interchangeably herein.

In view of this, one embodiment of the present invention provides use of a compound represented by formula (1) in preparing a medicine for treating or preventing ischemic optic neuropathy, wherein the formula (1) is as below:

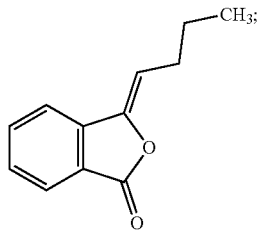 [SMILES: CCC/C=C1\OC(=O)c2ccccc21]

As used, the terms "compound represented by formula (1)" and "n-butylidenephthalide" refer to the same compound and are used interchangeably herein. The compound represented by formula (1) can be obtained by chemical synthesis, be commercially available or be extracted from plants such as, but not limited to, Angelica.

As used, the term "ischemic optic neuropathy" refers to the impairment of the optic nerve caused by ischemia and hypoxia of the optic nerve due to dysregulation of the blood vessels supplying the optic nerve. According to the affected area, it can be divided into anterior ischemic optic neuropathy and posterior ischemic optic neuropathy. Examples of anterior ischemic optic neuropathy may be, but are not limited to, arteritic anterior ischemic optic neuropathy, secondary vasculitis, nonarteritic anterior ischemic optic neuropathy, or secondary non-inflammatory small vessel disease.

The term "treatment" as used means the effect of reducing, ameliorating, or alleviating the symptoms of ischemic optic neuropathy by administration of medicines; the term "prevention" as used means the effect of inhibiting or delaying the symptoms of ischemic optic neuropathy by administration of medicines. Specifically, the medicine may be administered to an individual in need thereof for therapeutic or prophylactic purposes. More specifically, the medicine may be administered to an individual in need thereof for therapeutic or prophylactic purposes by protecting retinal ganglion cells, avoiding loss of visual function, alleviating optic disc swelling, maintaining the thickness of the retinal nerve fiber layer, reducing apoptotic cells in the retinal ganglion cell layer, reducing macrophage infiltration into the optic nerve, preventing demyelination, and/or regulating the NF-κB inflammatory signaling pathway. Examples of the individual may be, but are not limited to, mammals; examples of mammals may be, but are not limited to, primates, cats, dogs, mice, rats, rabbits, cattle, horses, goats, sheeps, or pigs; examples of primates may be, but are not limited to, chimpanzees, humans, gorillas, bonobos, orangutans, or monkeys.

The term "administration" is used to mean the introduction of a medicine into an individual by suitable means, examples of which may be, but are not limited to, oral, sublingual, rectal, nasal, vaginal, intraperitoneal, transdermal, epidermal, intra-articular, intra-ocular, or ocular surface administration. Depending on the manner of administration, the medicine may be in different dosage forms such as, but not limited to, lozenges, capsules, granules, solutions, emulsions, suppositories, patches, eye drops, implants, or powders. Specifically, the medicine may be administered to the individual in need thereof at 0.8-100 mg of the compound represented by formula (1) per kg of individual's body weight for therapeutic or prophylactic purposes, and preferably at 1.6-10 mg per kg of individual's body weight. Specifically, the medicine may be administered once to six times a day for 5 to 14 consecutive days to an individual in need thereof for therapeutic or prophylactic purposes, preferably once to three times a day for 5 to 10 consecutive days, and more preferably once a day for 7 consecutive days.

The dose of the compound represented by formula (1) is related to the species of the individual. Under the condition where the individual is a rat, the compound represented by formula (1) is administered at a dose of 5 mg to 50 mg per kg of body weight of the rat, preferably 10 mg per kg of body weight of the rat. Based on this, in conjunction with the guideline "Estimating the Maximum Safe Starting Dose in Initial Clinical Trials for Therapeutics in Adult Healthy Volunteers" issued by the US Food and Drug Administration, the following doses can be worked out: under the condition where the individual is a human, the dose of the compound represented by formula (1) is 0.8 mg to 8 mg per kg of body weight of the human, and preferably 1.6 mg per kg of body weight of the human; under the condition where the individual is a mouse, the dose of the compound represented by formula (1) is 9.84 mg to 98.4 mg per kg of body weight of the mouse, and preferably 19.68 mg per kg of body weight of the mouse; under the condition where the individual is a rabbit, the dose of the compound represented by formula (1) is 2.48 mg to 24.8 mg per kg of body weight of the rabbit, and preferably 4.96 mg per kg of body weight of the rabbit; under the condition where the individual is a dog, the dose of the compound represented by formula (1) is 1.44 mg to 14.4 mg per kg of body weight of the dog, and preferably 2.88 mg per kg of body weight of the dog; under the condition where the individual is a monkey, the dose of the compound represented by formula (1) is 2.48 mg to 24.8 mg per kg of body weight of the monkey, and preferably 4.96 mg per kg of body weight of the monkey.

The present invention is illustrated by the following examples:

Experimental Example 1

Animal Experiment

All the animal experiments were approved by the Institutional Animal Care and Use Committee (IACUC) of Tzu Chi University. Animal experimental procedures in vision research were implemented on the basis of the ARVO Statement.

Figure 2:
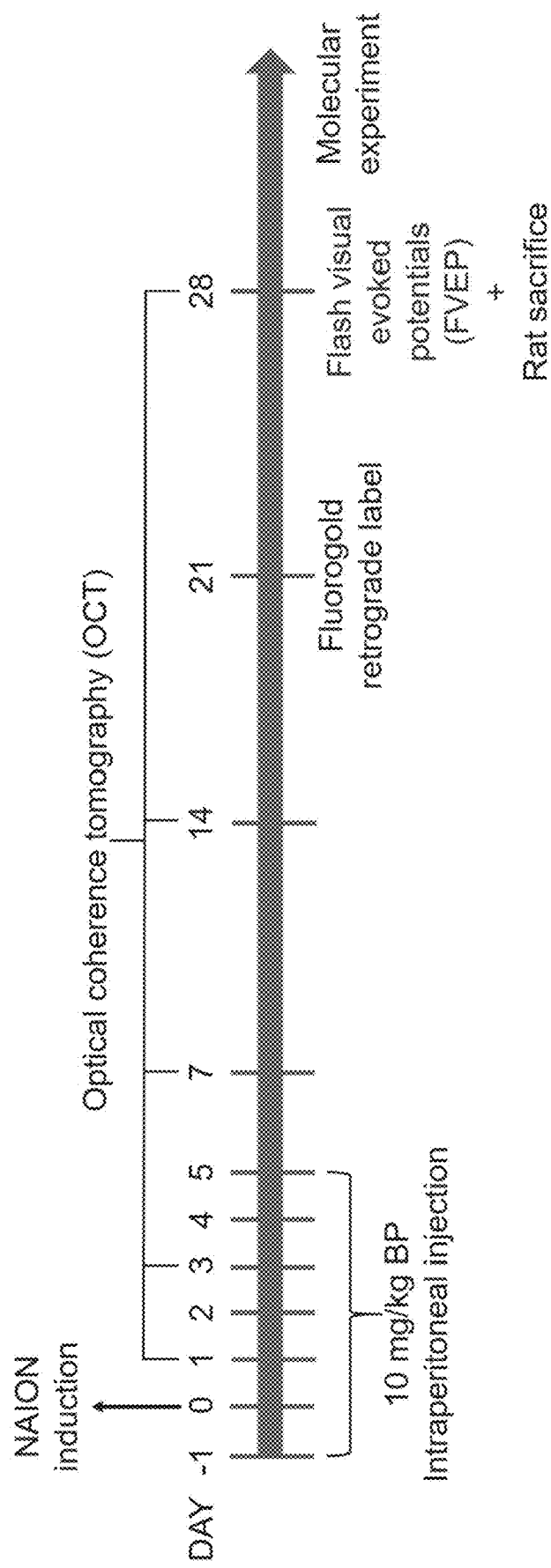
FIG. 2 is a schematic diagram showing the experimental procedure of an animal model of ischemic optic neuropathy.

Adult male Wistar rats of 4 to 6 weeks of age (weighing 100-125 g) were used in the animal model of ischemic optic neuropathy and were divided into three groups: the sham group, the group administered with PBS following ischemic optic neuropathy injury, and the group with ischemic optic neuropathy injury accompanied by intraperitoneal injection of BP at 10 mg/kg for 7 consecutive days. The rats were housed in an animal room having a 12-hour light/dark cycle (the light cycle time is from 7 a.m. to 7 p.m.) with temperature controlled at 23° C. and humidity controlled at 55%, and supplied with filtered sterilized water and general rodent feed. During the experiment, general anesthesia of rats was performed by intramuscular injection of ketamine at 100 mg/kg and xylazine at 10 mg/kg. Local anesthesia was performed by using 0.5% Alcaine, and mydriasis was performed by administering Mydrin-P. To sacrifice the rats, carbon dioxide at a filling rate of 5 L/min was injected so that the volume of carbon dioxide was 20% of that of the cage, thereby achieving the main goal of reducing animal suffering. The timeline of the experimental process is shown in FIG. 2.

Experimental Example 2

AION Induction

Firstly, under local anesthesia, rats were administrated with Alcaine and Mydrin-P eye drops to induce mydriasis. Subsequently, the rats were intravenously injected with rose bengal (2.5 mM dissolved in PBS at pH 7.4) at 1 mL/kg, and immediately irradiated with 12 pulses (once per second) of argon green laser (wavelength: 532 nm, size: 500 mm, power: 80 mW) to excite various parts of the optic disc. In addition, the laser was focused on the optic disc by an ophthalmoscope. Then, Tobradex eye ointment was applied evenly to the rats' eyes. Finally, the physical health of the rats was taken care of daily until the end of the study.

Experimental Example 3

Retrograde Labeling of RGCs with FluoroGold (FG)

Retrograde labeling was performed three weeks after the rats were AION induced. The sagittal plane of the skull was used as the position coordinate, and 2 µL of 5% Fluorogold was injected into the superior colliculus (anteroposterior: −6 mm; dorsoventral: ±1.5 mm; medial-lateral: −4 mm). One week after labeling, the rats were sacrificed and the eyeballs were carefully removed from the abdomen and fixed in 10% formalin for 2 hours. The entire retina was placed flat on a slide and paired with a filter set (excitation filter: 350-400 nm; radiation filter: 515 nm) and observed for morphology under a fluorescence microscope. The region with a radius of 1 mm from the center of the retina is defined as the central region, and the region with a radius of 3 mm from the center is defined as the mid-peripheral region. Ten blocks (38,250 $\mu m^2$; 225 µm×170 µm) were randomly selected from the central region and the mid-peripheral region to estimate the density of RGCs to determine the survival rate of RGCs.

Experimental Example 4

Flash Visual Evoked Potential (FVEP)

Twenty-eight days after AION induction, electrodes were implanted into the primary visual cortex (anteroposterior: −8 mm; dorsoventral: ±3 mm) and frontal cortex (anteroposterior: +1 mm), while a ground electrode was implanted in the tail. The visual electrical diagnostic system was set as follows: no background lighting; global scintillation intensity of 0 db; single flash rate of light of 1.9 Hz; threshold to exclude artifact of 20 mV; and sampling frequency of 2000 Hz. After the measurement, the average value of 100 scans was taken. The entire recording process was performed in a dark room. The general visual function was evaluated by P1-N2 amplitude.

Experimental Example 5

Immunohistochemistry (IHC)

First, vertical-sections of the ON were blocked with 2% bovine serum albumin (BSA) containing 0.3% triton X-100 for 1 hour. The ON tissue and primary antibody anti-ED1 antibody and anti-2',3'-cyclic-nucleotide 3'-phosphodiesterase (CNPase) antibody were incubated overnight at 4° C. Goat anti-mouse Alexa Fluor 488 antibody was used as a secondary antibody and incubated with the sections at room temperature for 1 hour. Fluorescence photographs of the sections of the ON tissue were taken at 10× magnification and 20× magnification using the Zeiss LSM 900 confocal system. The 20× magnified image of ED1$^+$ cells was analyzed using ImageJ software for quantification of exogenous macrophages.

Experimental Example 6

Terminal Deoxynucleotidyl Transferase dUTP Nick End Labeling (TUNEL) Assay

Apoptotic cells in the ganglion cell layer (GCL) were detected using TUNEL assay according to the manufacturer's protocol. TUNEL-positive cells were calculated manually based on at least 6 retinal sections per eyeball in three groups (n=6 for each group).

Experimental Example 7

Optical Coherence Tomography (OCT) Imaging

On days 1, 3, 7, 14, and 28 after AION induction, the optic nerve width (ONW) and the coherence tomography image of the retinal nerve fiber layer (RNFL) were obtained using a Micron IV retinal microscope. The vertical resolution and horizontal resolution of the imaging system were set to be 1.8 µm and 3 µm, respectively, to provide a 3.2 mm field of view and 1.2 mm depth of field for the retina. The cornea was moistened with Methocel 2%. The Micron eyepiece was glued to be in direct contact with the eye. To allow vertical light penetration through the cornea, the retinal nerve fiber layer and the Bruch's membrane opening (ONW) were imaged with circular and linear scans, respectively, with an average of 50 frames per scan.

Experimental Example 8

Western Blotting Analysis

The detailed process of Western blotting process was described in the inventors' previous articles Cell Death Dis. 2017, 8, e3172 and Nat. Med. 2015, 21, 677-687. The total protein of the rat retina was extracted with modified radio immunoprecipitation assay (RIPA) buffer, and the protein concentrations were analyzed using the bicinchoninic acid (BCA) protein assay kit. The 50 μg retinal protein extracts was separated on either 8% or 10% sodium dodecyl sulfate polyacrylamide gels (SDS-PAGE) and transferred to polyvinylidene difluoride (PVDF) membrane. The membrane was blocked with a buffer containing 5% skim milk dissolved in TBST for 2 hours at room temperature and then incubated overnight at 4° C. with primary antibodies anti-NF-κB antibody, anti-phospho-NF-κB antibody, anti-IκBα antibody, anti-phospho-IκBα antibody, anti-NLRP3 antibody, anti-IL-1β antibody and anti-GAPDH antibody. The membrane was washed with TBST, and then incubated with the corresponding horseradish peroxidase (HRP) conjugated secondary antibody for 2 hours at room temperature. The protein signal on the membrane was detected using an enhanced chemiluminescence (ECL) kit. The signal strength of the bands was quantified using ImageJ software.

Analysis Example 1

BP Rescued RGC Survival Rates

Figure 3A:
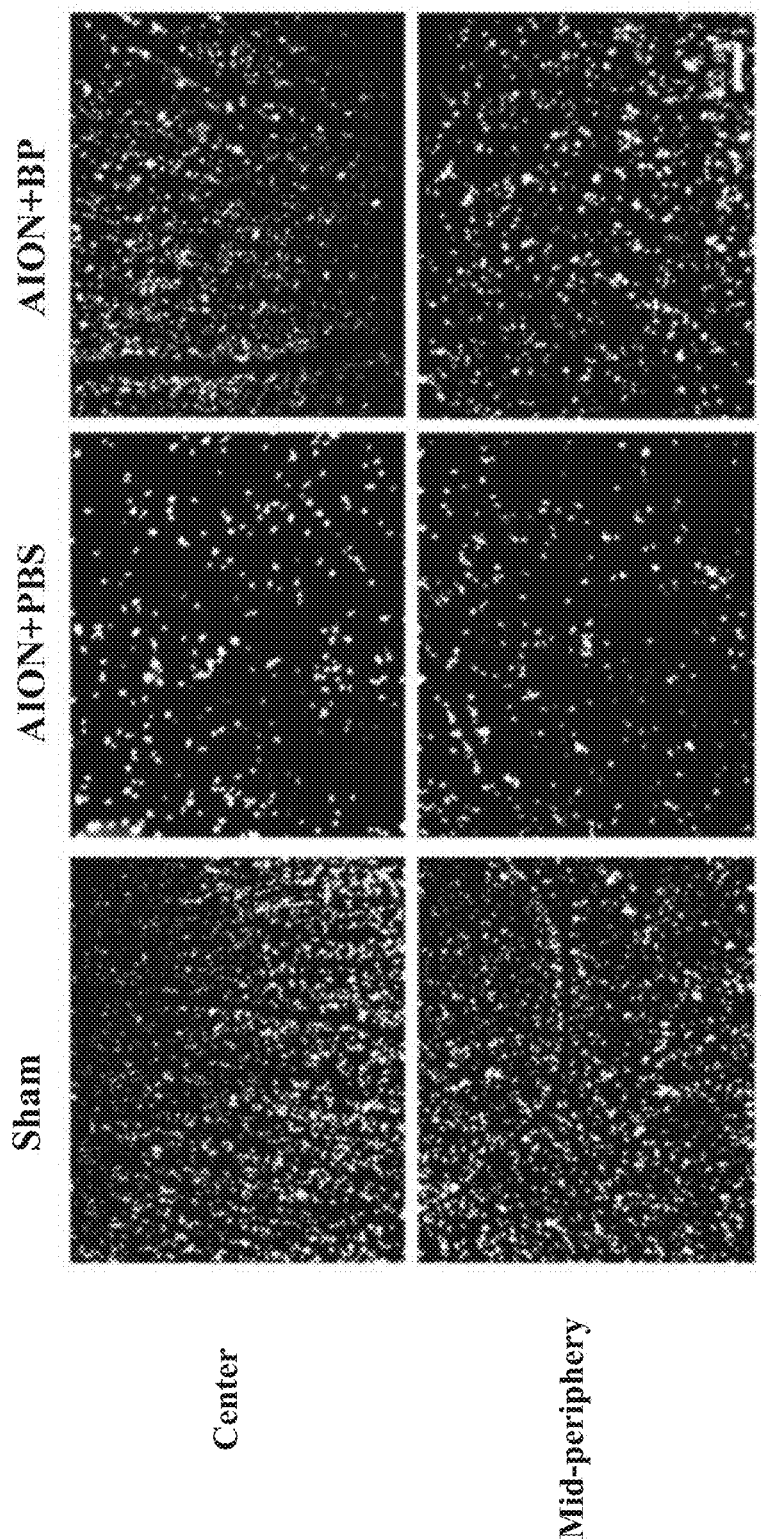
FIG. 3A is a photograph showing the effects of different treatments on the survival of retinal ganglion cells in the central and mid-peripheral regions.
Figure 3C:
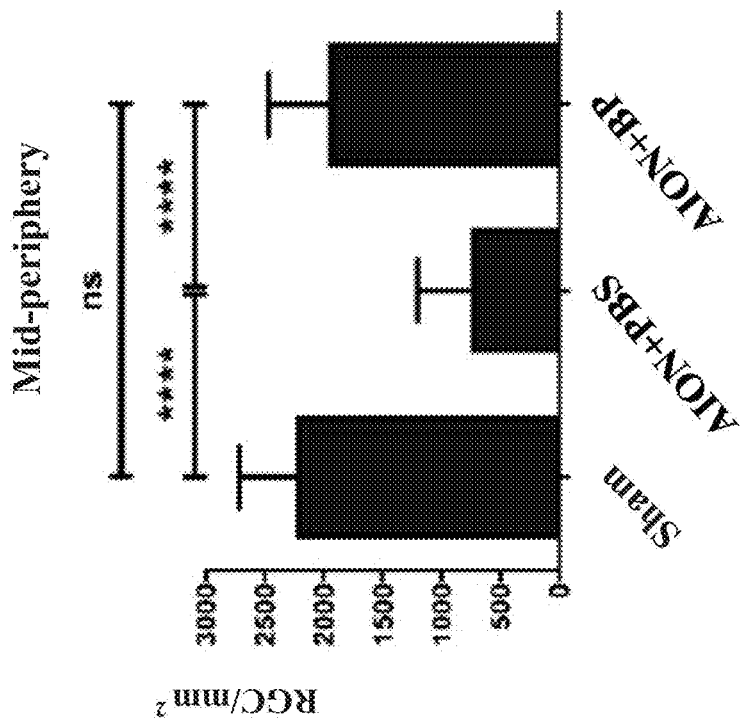
FIG. 3C is a bar chart illustrating the density of RGCs in the mid-peripheral region with different treatments.
Figure 3B:
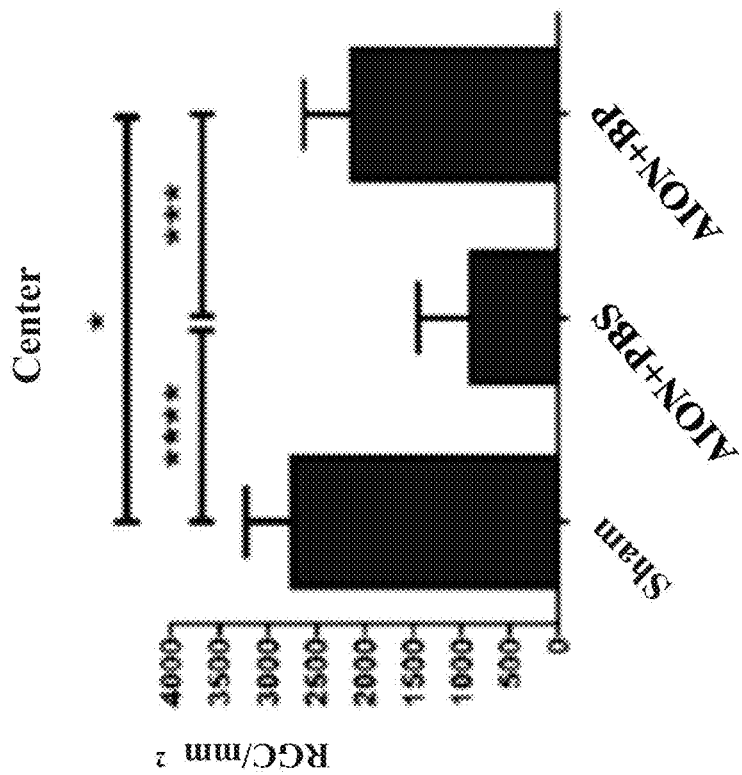
FIG. 3B is a bar chart illustrating the density of retinal ganglion cells in the central region with different treatments.

To investigate the effect of BP on RGC survival rates after AION induction, retrograde labeling was carried out using Fluorogold (FG). As shown in FIG. 3A to FIG. 3C, in the sham group, there were 2771±453 and 2236±487 RGCs per $mm^2$ in the central and mid-peripheral regions, respectively. After AION induction, there were 935±514 and 2172±458 RGCs per $mm^2$ in the central retina for the PBS-treated group and the BP-treated group, respectively. In addition, there were 750±452 and 1962±505 RGCs per $mm^2$ in the mid-peripheral retina for the PBS-treated group and the BP-treated group, respectively. As can be seen, BP can significantly improve the survival rate by 44.7% and 54.2% respectively in the central retina and the mid-peripheral retina in the rodent model of NAION, which indicates that BP has neuroprotective effects on RGCs.

Analysis Example 2

BP Preserved the Visual Function

Figure 4A:
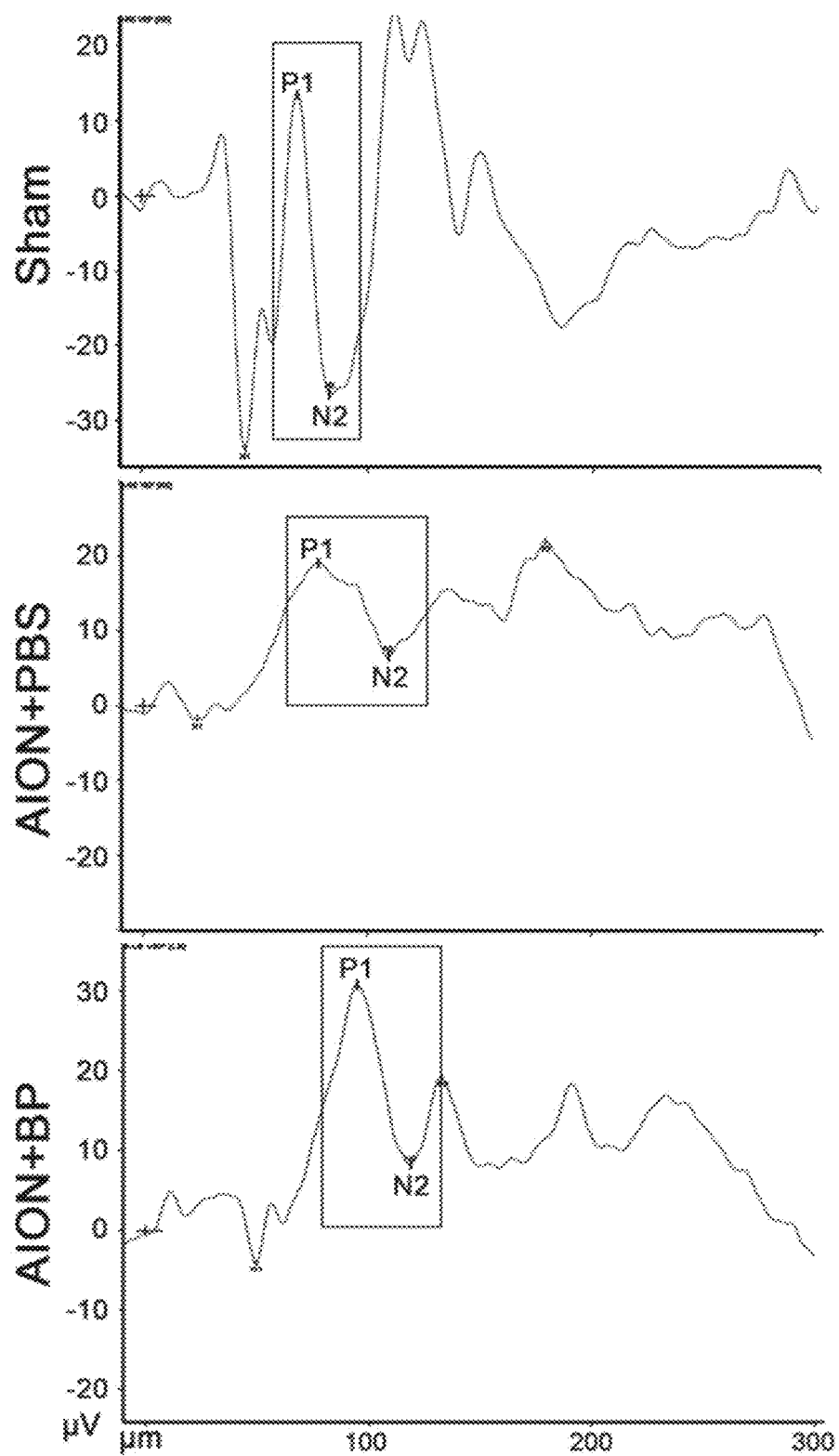
FIG. 4A is a curve diagram showing the effects of different treatments on FVEPs.
Figure 4B:
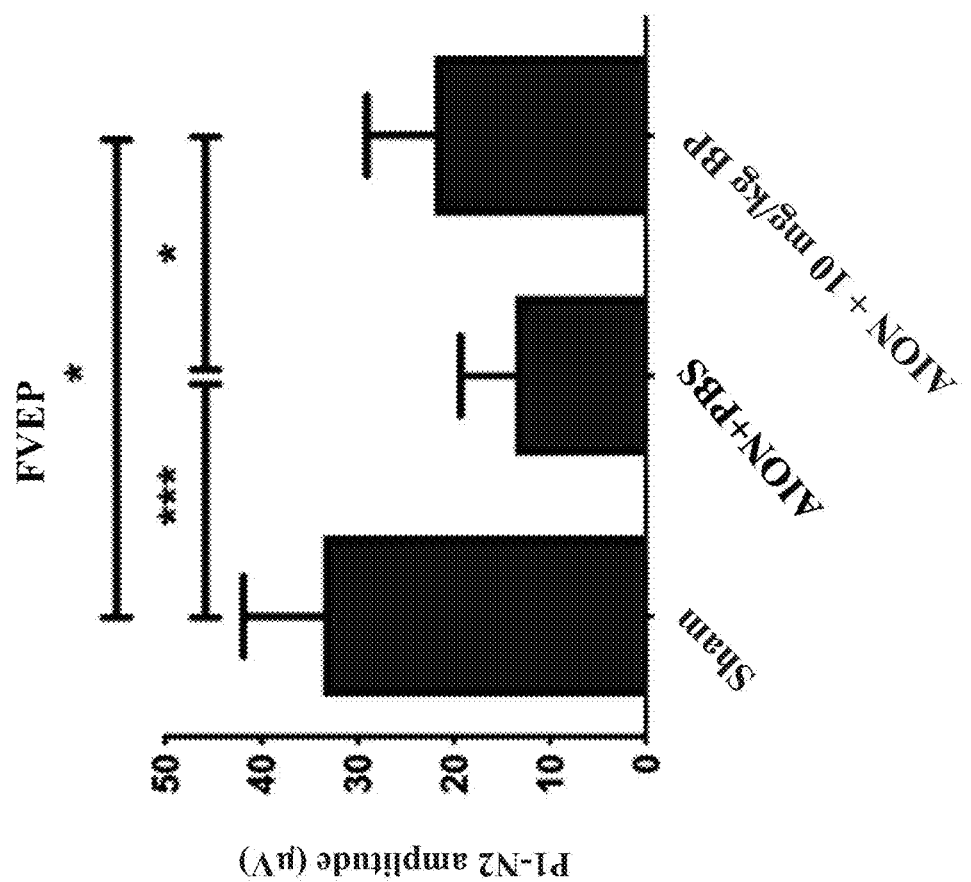
FIG. 4B is a bar chart illustrating difference in potential for P1 to N2 amplitudes with different treatments.

To measure the voltage of P1 to N2, the rats were subjected to visual light stimulation from flash visual evoked potentials (FVEPs). As shown in FIG. 4A to FIG. 4B, the amplitudes of the sham group, PBS-treated group, and BP-treated group were 33.63±8.30 μV, 13.70±5.59 μV, and 22.01±7.03 μV, respectively. The above results indicate that BP can avoid the loss of visual function after ischemic injury.

Analysis Example 3

BP Mitigated Optic Disc Edema and Preserved RNFL Thickness

Figure 5A:
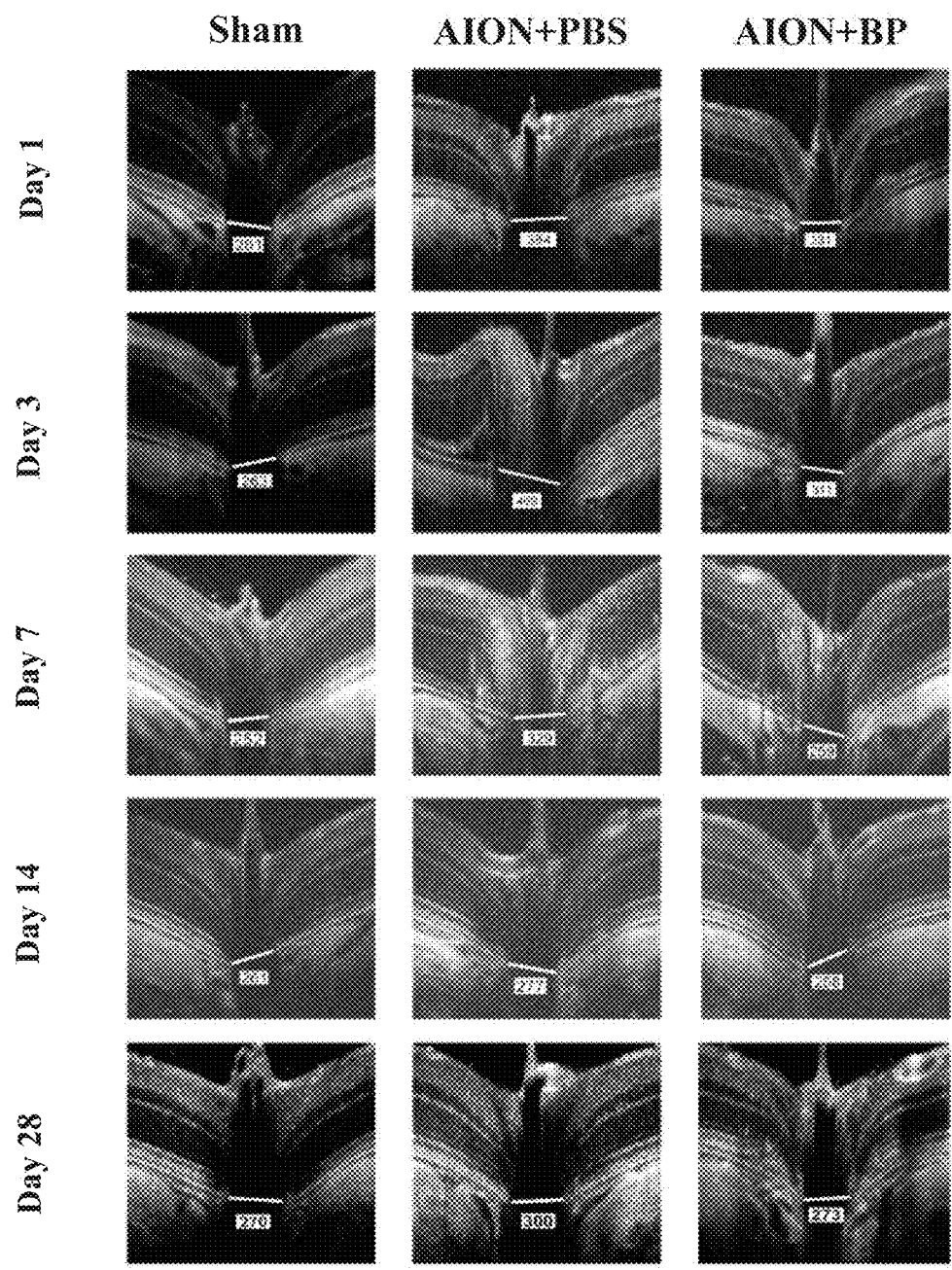
FIG. 5A is a photograph showing the effect of different treatments on optic nerve width.
Figure 5B:
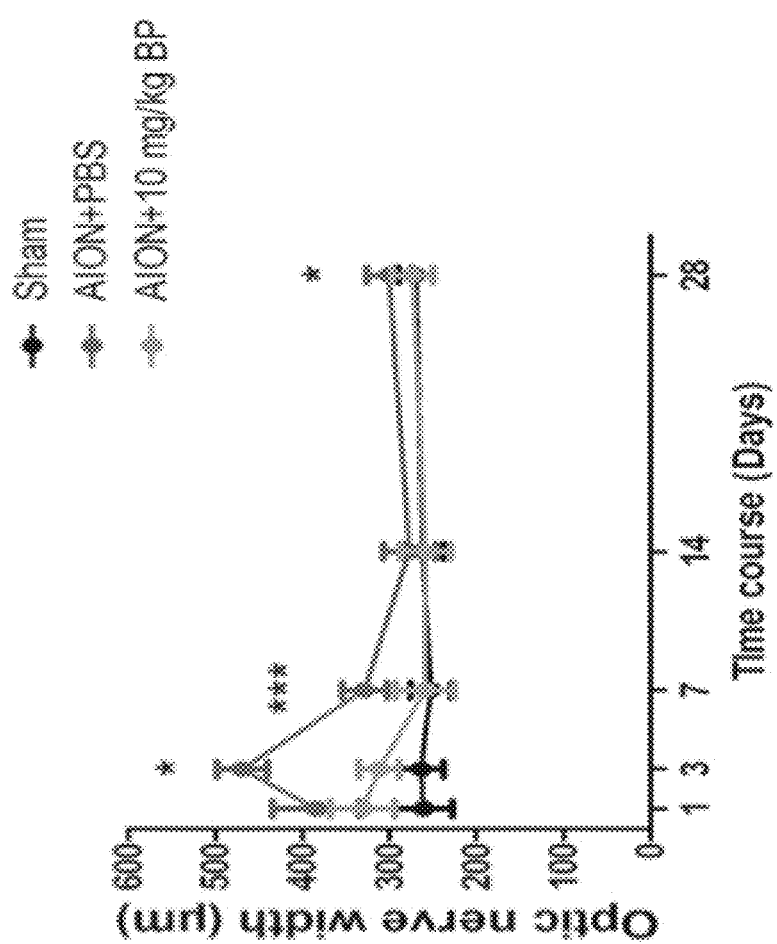
FIG. 5B is a curve diagram illustrating optic nerve width with different treatments.
Figure 6A:
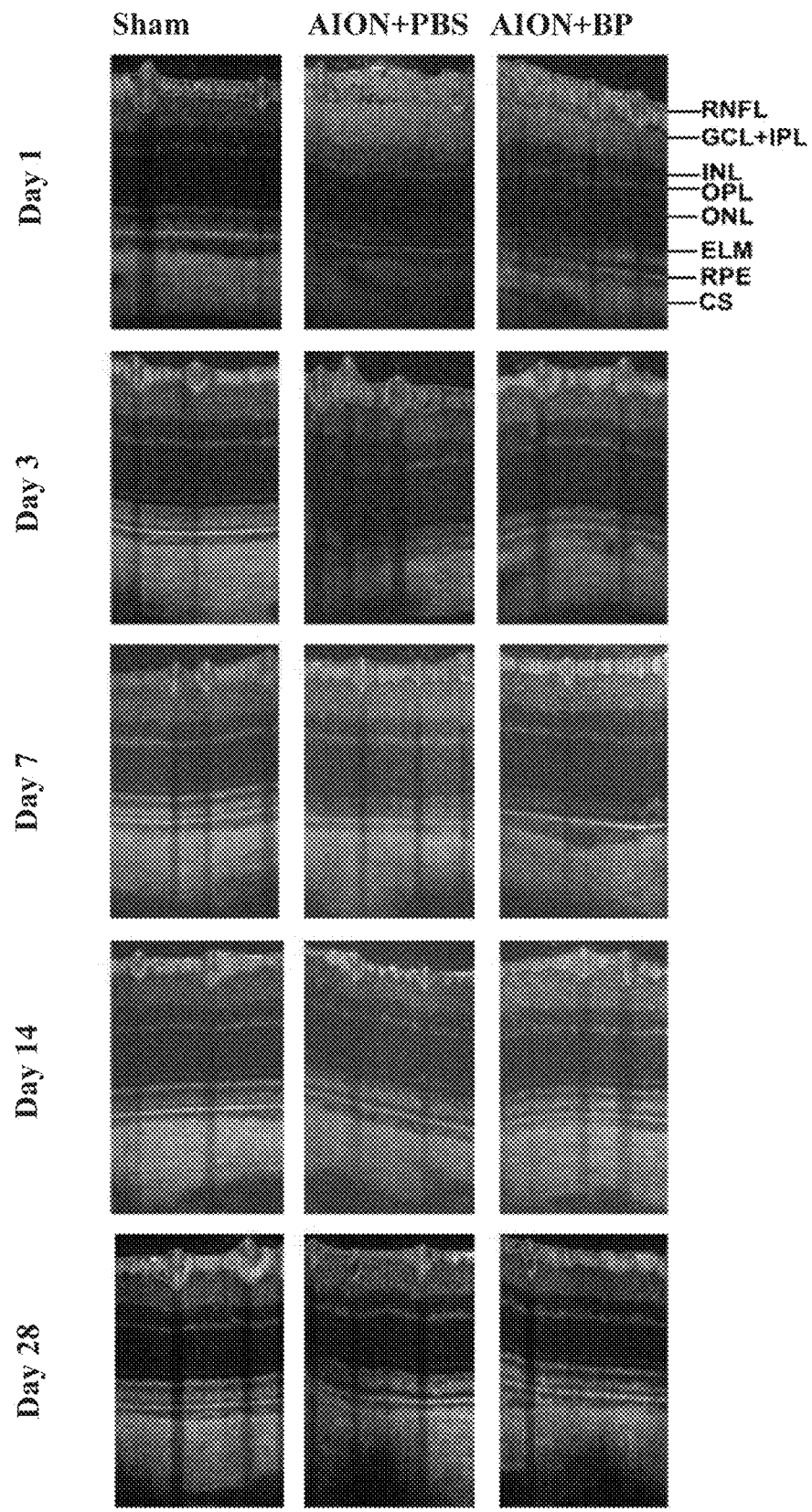
FIG. 6A is a photograph showing the effects of different treatments on the appearance of the RNFL.
Figure 6B:
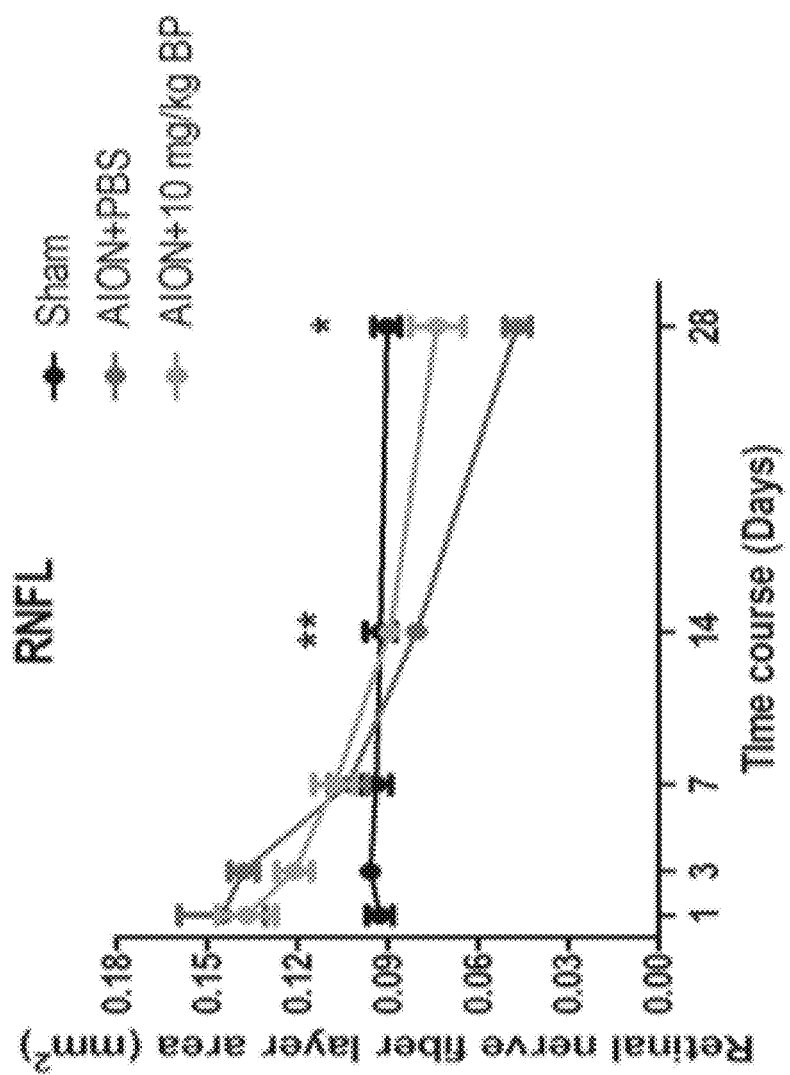
FIG. 6B is a curve diagram illustrating the area of the retinal nerve fiber layer with different treatments.

The optic nerve width (ONW) and retinal nerve fiber layer (RNFL) thickness were measured on days 1, 3, 7, 14, and 28 using optical coherence tomography (OCT) imaging in the sham group, PBS-treated group, and BP-treated group. As shown in FIG. 5A and FIG. 5B, after AION induction, optic disc swelling can clearly observed in the acute onset stage, and it was improved by administration of BP on days 3, 7 and 28 (311.95±23.21 μm vs. 469.58±29.35 μm, 259.35±33.73 μm vs. 329±25.73 μm, 273.71±23.22 μm vs. 300.73±26.41 μm, respectively). The appearance of the RNFL was measured, and the results were shown in FIG. 6A and FIG. 6B. Compared with the PBS-treated group, BP was efficient in maintaining the area of the RNFL (0.089±0.0027 $mm^2$ vs. 0.08±0.0028 $mm^2$, 0.074±0.0089 $mm^2$ vs. 0.047±0.0042 $mm^2$ respectively) on days 14 and 28.

Analysis Example 4

BP Reduced Apoptotic Cells in the RGC Layer

Figure 7A:
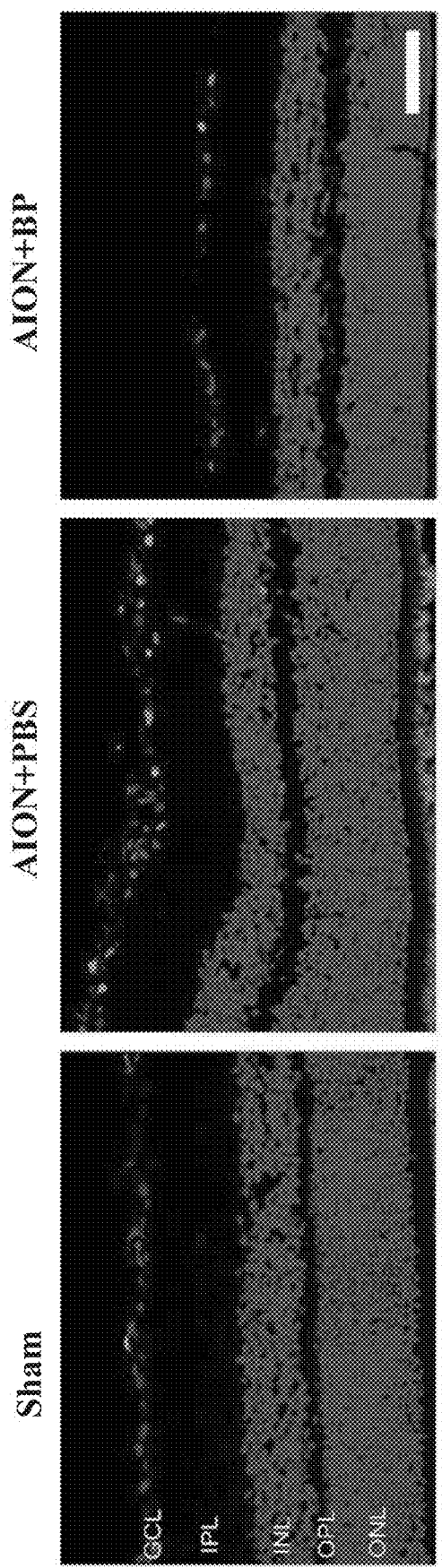
FIG. 7A is a photograph showing the effects of different treatments on apoptosis in the RGC layer.
Figure 7B:
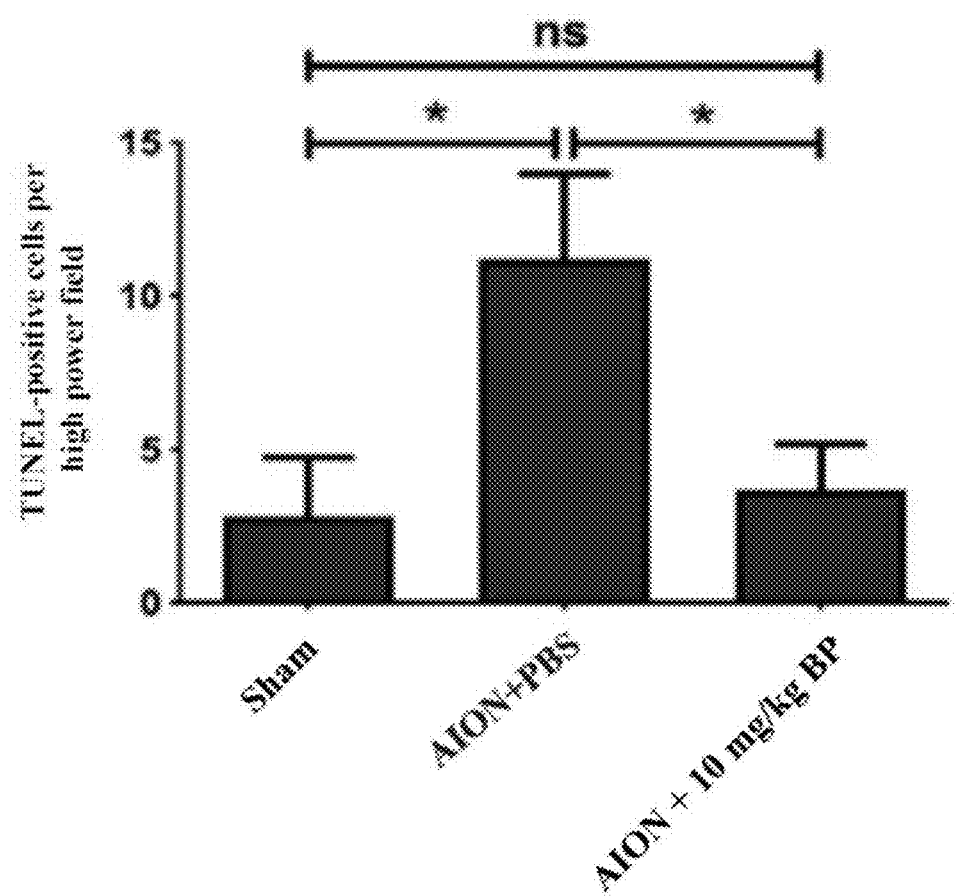
FIG. 7B is a bar chart illustrating the number of TUNEL-positive cells in the retinal ganglion cell layer with different treatments.

The terminal deoxynucleotidyl transferase dUTP nick end labeling (TUNEL) assay was used to analyze the apoptosis situation in the RGC layer. As shown in FIG. 7A and FIG. 7B, under each high powered field (HPF), there were 2.8±1.9, 11.2±2.8, and 3.7±1.5 TUNEL-positive cells in the sham group, PBS-treated group, and BP-treated group, respectively. After AION induction, the PBS-treated group can significantly increase the apoptosis of RGCs, whereas the TUNEL-positive cell count was decreased in the BP-treated group, which indicates that BP had an antiapoptotic effect in the rAION model.

Analysis Example 5

BP Reduced Macrophage Infiltration Into the Optic Nerve from the Blood

Figure 8A:
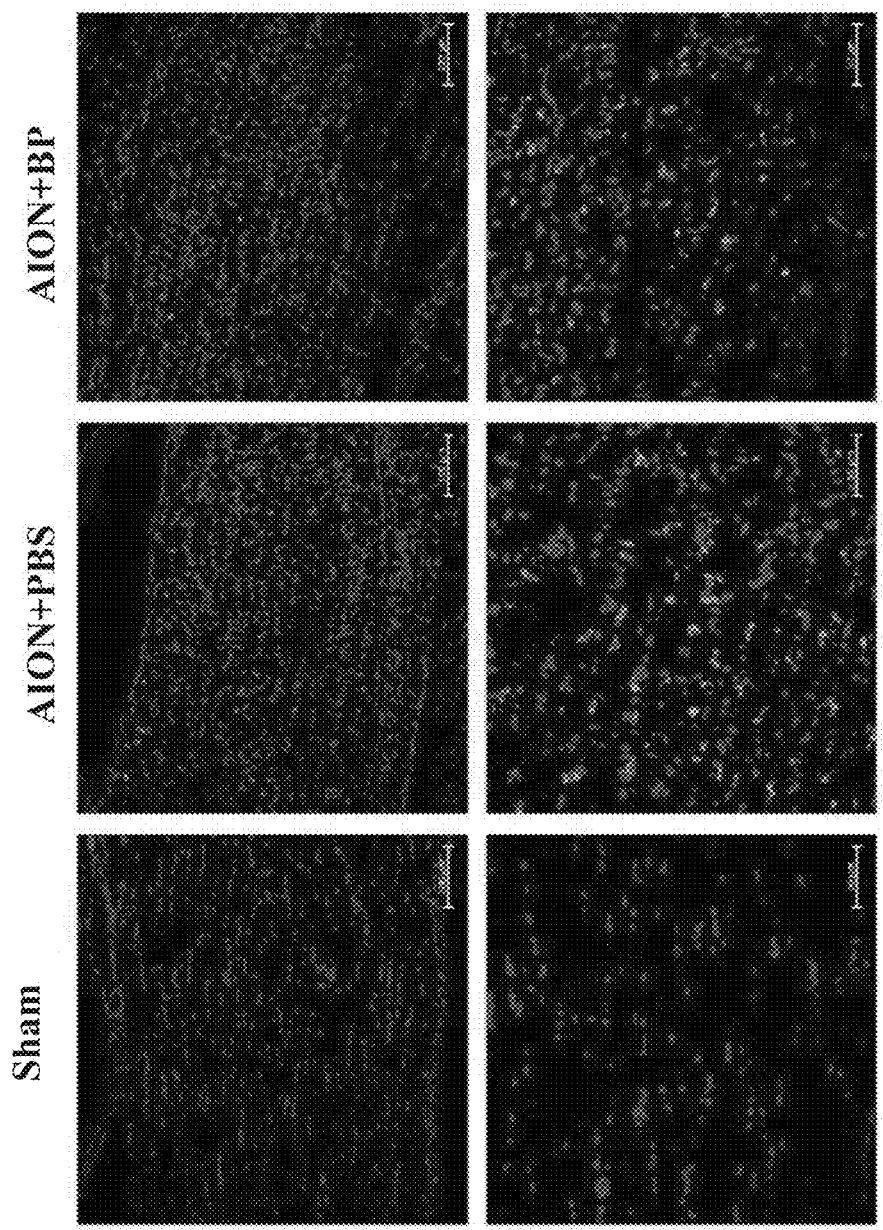
FIG. 8A is a photograph showing the effects of different treatments on ED1$^+$ macrophage infiltration.
Figure 8B:
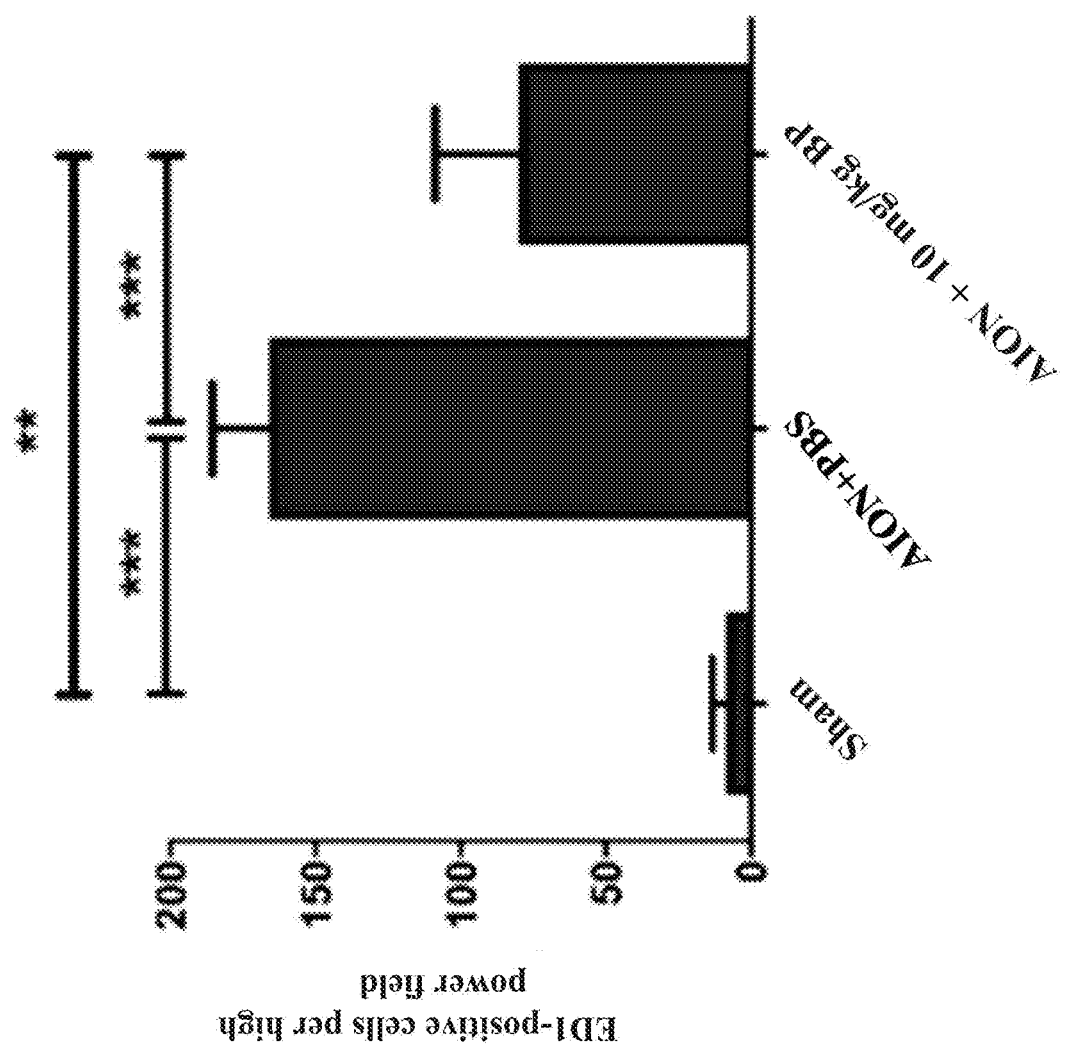
FIG. 8B is a bar chart illustrating the number of ED1$^+$ macrophages with different treatments.

After AION induction, the inflammatory response of $ED1^+$ blood-borne macrophages in the ON may cause ON damage. Here, we investigated whether BP inhibits $ED1^+$ macrophage infiltration in the rAION model. As shown in FIG. 8A to FIG. 8B, under each high powered field, there were 8.7±4.8, 166.4±19.3 and 80.1±28.9 ED1-positive cells in the sham, PBS-treated, and BP-treated groups, respectively. The results of immunohistochemistry (IHC) indicate that BP treatment had an anti-inflammatory effect by reducing the accumulation of $ED1^+$ macrophages in the ONs.

Analysis Example 6

BP Preserved Myelin Integrity in the rAION Model

Figure 9A:
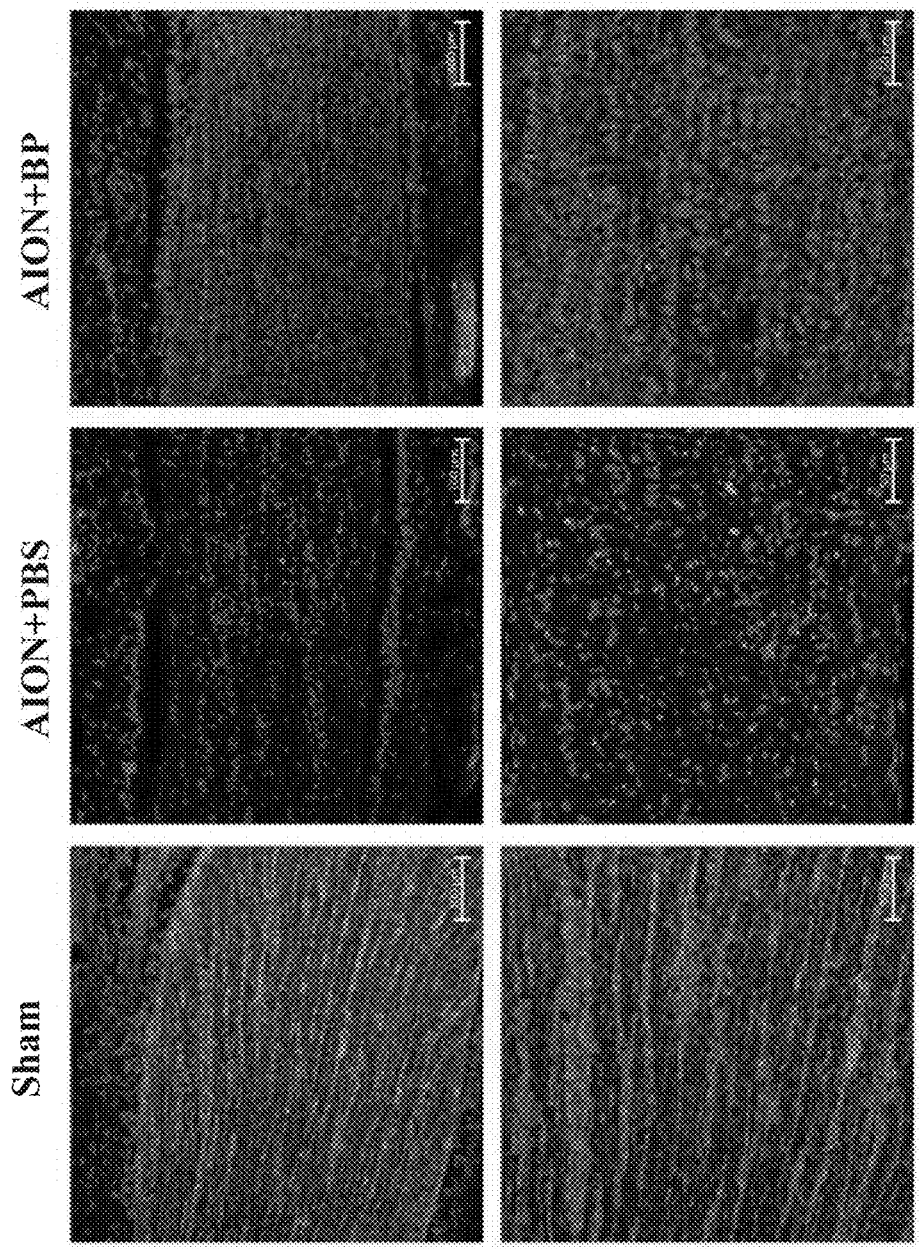
FIG. 9A is a photograph showing the effects of different treatments on myelin integrity.
Figure 9B:
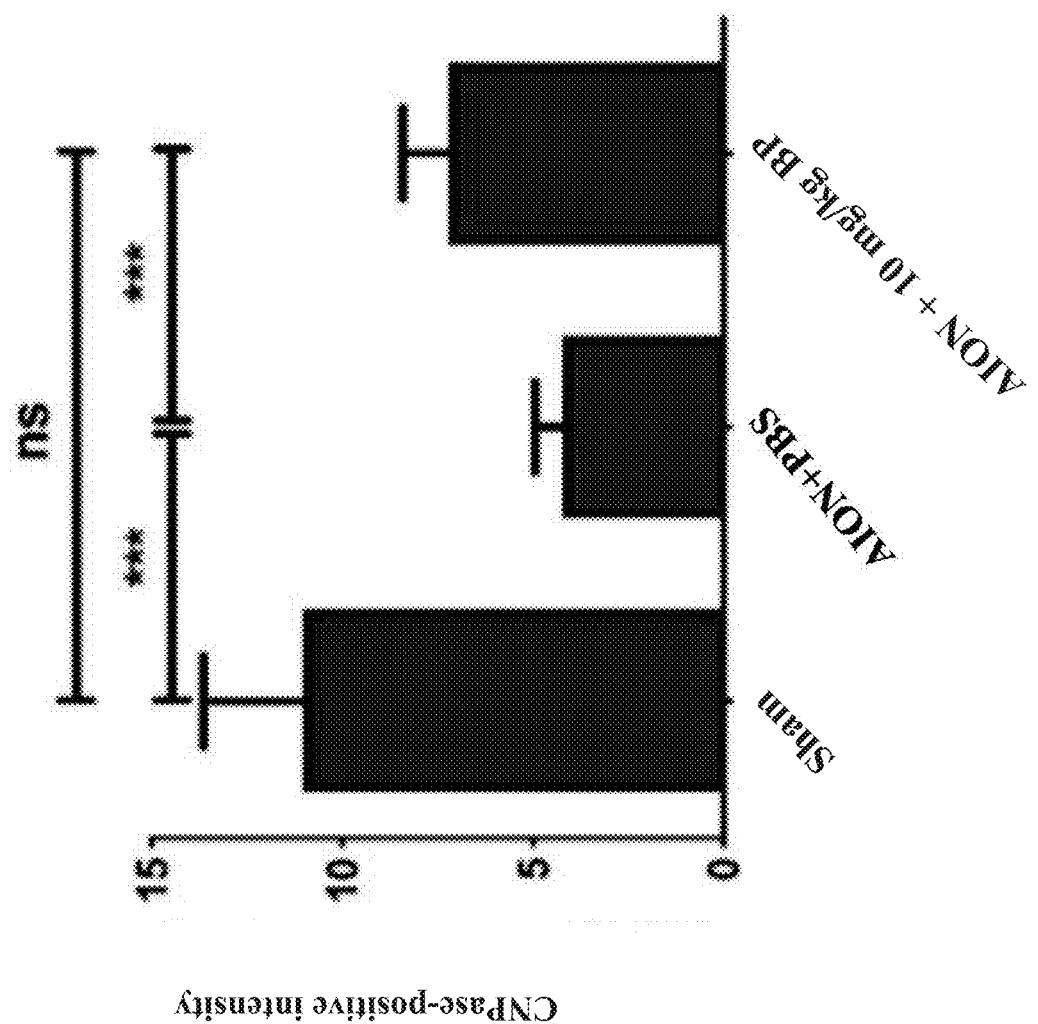
FIG. 9B is a bar chart illustrating the expression level of CNPase with different treatments.
Figure 10A:
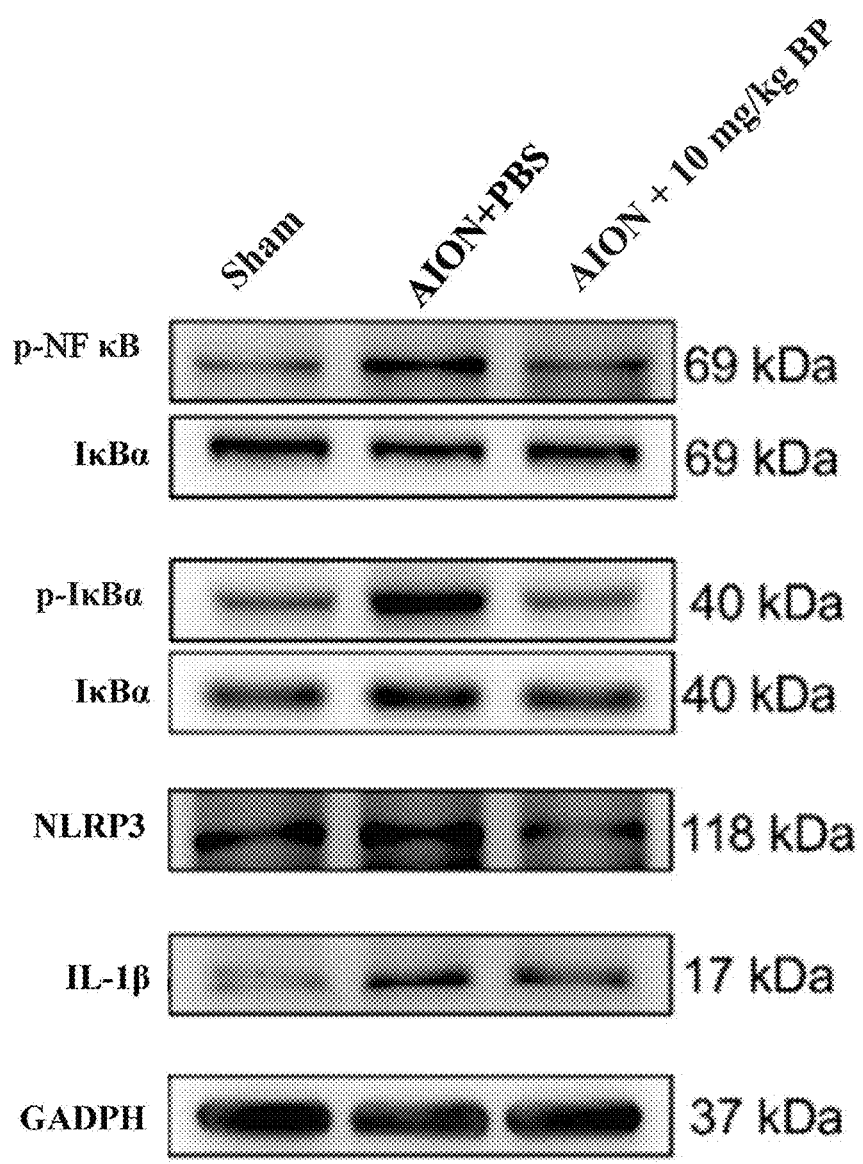
FIG. 10A is a photograph showing the effects of different treatments on activation of various factors.
Figure 10C:
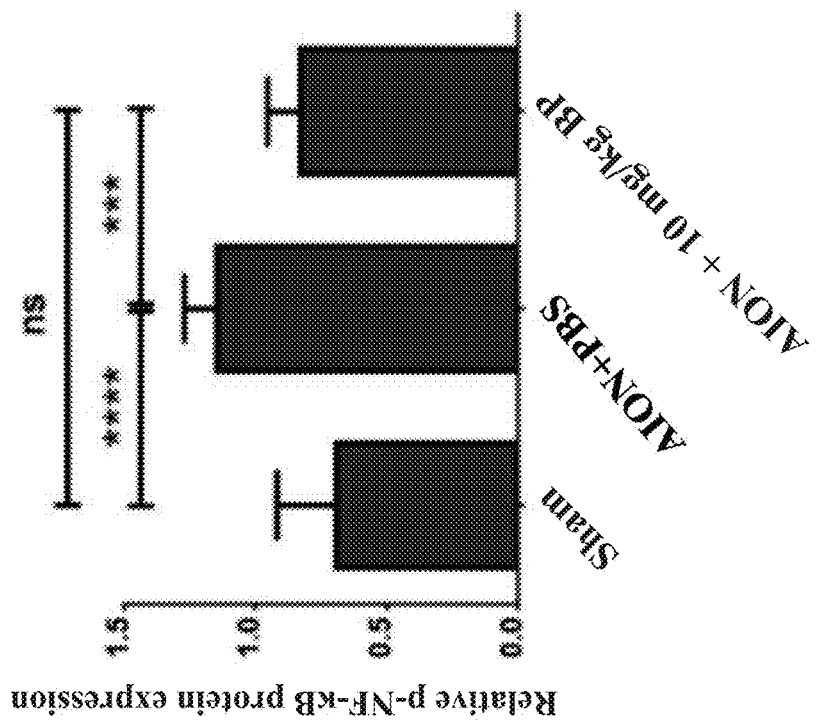
FIG. 10C is a bar chart illustrating the expression level of phospho-NF-κB with different treatments.
Figure 10B:
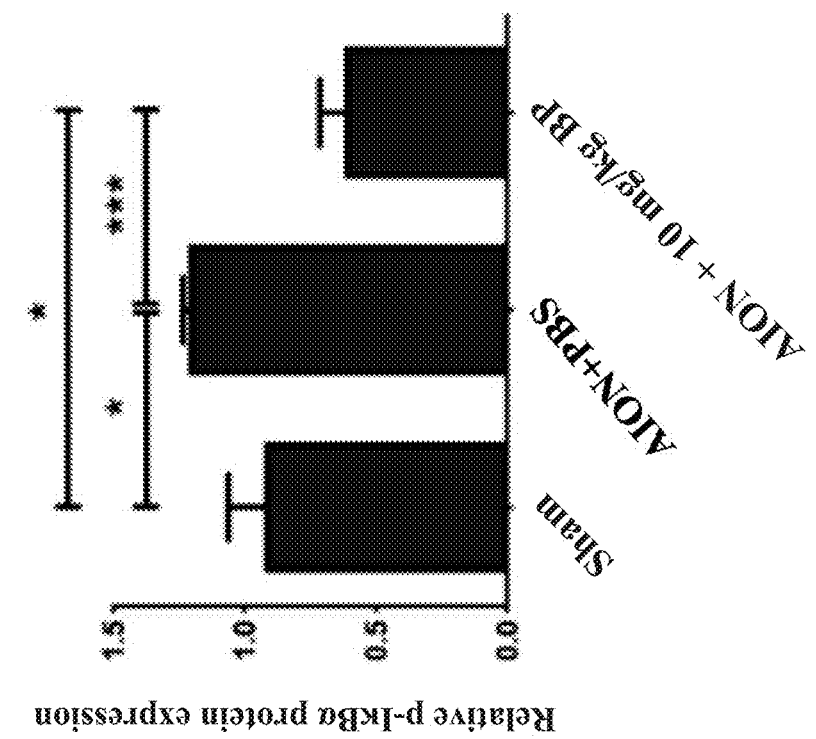
FIG. 10B is a bar chart illustrating the expression level of phospho-IκBα with different treatments.
Figure 10E:
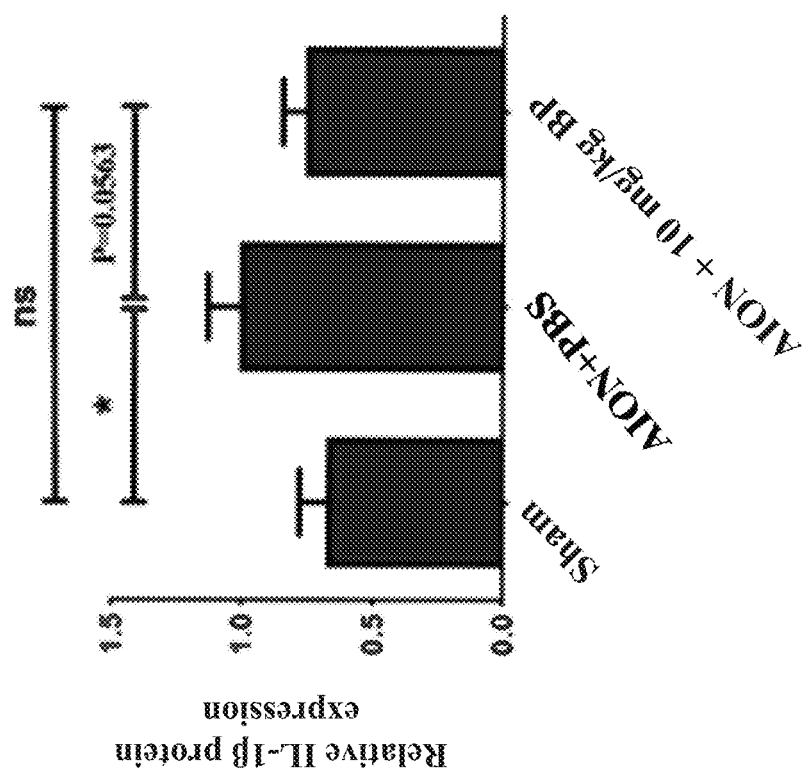
FIG. 10E is a bar chart illustrating the expression level of IL-1β with different treatments.
Figure 10D:
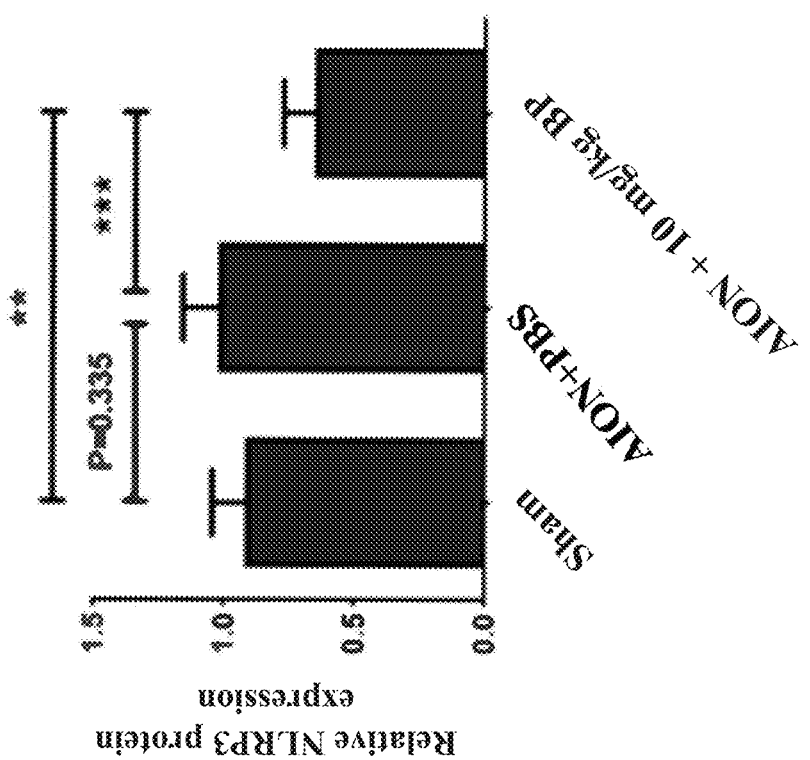
FIG. 10D is a bar chart illustrating the expression level of NLRP3 with different treatments.

CNPase is involved in the process of myelination and is one of the important components of the cytoskeleton of oligodendrocytes. Demyelination is one of the main signs of many neurodegenerative diseases. Here, we studied the level of CNPase in a rAION model to assess myelin integrity. As shown in FIG. 9A to FIG. 9B, the results of immunohistochemistry indicate that the signal of CNPase was significantly expressed in the sham group (11.06±2.60). After AION induction, relatively significantly lower CNPase expression (4.24±0.71) and less severe destruction of myelin structures in the ON tissue were observed. In contrast, administration of BP can both increased the expression of CNPase (7.20±1.22) and retained the integrity of the myelin. In short, administration of BP in the rAION model can prevent demyelination and myelin dysfunction.

Analysis Example 7

BP Inhibited Inflammatory Response Through the NF-κB Signaling Pathway

Previous studies have pointed out that the upregulation of reactive oxygen species (ROS) in ischemic injury induces inflammatory response through the IκBa-NF-κB signaling pathway. Here, protein expression of the NF-κB-related pathway was evaluated to investigate the molecular mechanisms involved in the protection of nerves by administration of BP. In the rAION model, high expression of phospho-IκBα (p-IκBα) induces phospho-NF-κB (p-NF-κB) to translocate into the nucleus, which can activate inflammatory gene transcription and NLRP3 as well as IL-1β signaling. As shown in FIG. 10A to FIG. 10E, the BP-treated group significantly inhibited phosphorylation of IκBα and NF-κB and reduced expression of downstream inflammatory cytokines, NLRP3 and IL-1β as compared with AION+PBS group. The above results demonstrate that BP is capable of neuroprotevtive effects through modulation of the NF-κB inflammatory signaling pathway in the rAION model.

However, what described above are only preferred embodiments of the present invention and are not intended to limit the scope of the present invention. Therefore, simple equivalent changes and modifications made in accordance with the claims and the specification of the present invention are intended to be covered by the present invention.

What is claimed is:

1. A method for treating or preventing ischemic optic neuropathy, comprising:
    administering a medicine to an individual in need thereof, wherein the medicine comprises a compound represented by formula (1):

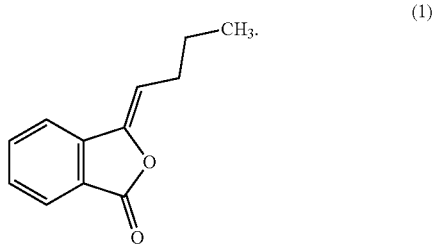 [SMILES: CCC/C=C1\OC(=O)c2ccccc21]

(1)

2. The method according to claim 1, wherein the ischemic optic neuropathy is anterior ischemic optic neuropathy or posterior ischemic optic neuropathy.

3. The method according to claim 2, wherein the anterior ischemic optic neuropathy is arteritic anterior ischemic optic neuropathy, secondary vasculitis, nonarteritic anterior ischemic optic neuropathy, or secondary non-inflammatory small vessel disease.

4. The method according to claim 1, wherein the medicine is administered to protect retinal ganglion cells, avoid loss of visual function, alleviate optic disc swelling, maintain the thickness of the retinal nerve fiber layer, reduce apoptotic cells in the retinal ganglion cell layer, reduce macrophage infiltration into the optic nerve, prevent demyelination, and/or modulate the NF-κB inflammatory signaling pathway.

5. The method according to claim 1, wherein the individual is a mammal.

6. The method according to claim 5, wherein the administration is oral, sublingual, rectal, nasal, vaginal, intraperitoneal, transdermal, epidermal, intra-articular, intraocular, or ocular surface administration.

7. The method according to claim 5, wherein the medicine is administered to the individual at 0.8-100 mg of the compound represented by formula (1) per kg of the individual's body weight.

8. The method according to claim 5, wherein the medicine is administered to the individual once to six times daily for 5 to 14 consecutive days.

9. The method according to claim 5, wherein when the individual is a human, the compound represented by formula (1) is administered in a dose of 0.8-8 mg per kg of body weight of the human.

10. The method according to claim 7, wherein the ischemic optic neuropathy is nonarteritic anterior ischemic optic neuropathy.

* * * * *